(12) United States Patent
Hammond

(10) Patent No.: US 6,216,091 B1
(45) Date of Patent: Apr. 10, 2001

(54) ULTRASONIC MEASUREMENT SYSTEM WITH MOLECULAR WEIGHT DETERMINATION

(75) Inventor: Robert H. Hammond, Cambridge, MA (US)

(73) Assignee: Panametrics, Inc., Waltham, MA (US)

( * ) Notice: Subject to any disclaimer, the term of this patent is extended or adjusted under 35 U.S.C. 154(b) by 0 days.

(21) Appl. No.: 09/405,864

(22) Filed: Sep. 24, 1999

Related U.S. Application Data

(60) Provisional application No. 60/101,756, filed on Sep. 25, 1998.

(51) Int. Cl.[7] ................... G01F 1/66; G01N 29/02
(52) U.S. Cl. .................. 702/23; 137/101.31; 700/282; 73/861.28
(58) Field of Search .................. 73/861.29, 861.28, 73/149; 137/101.31; 700/282; 702/23

(56) References Cited

U.S. PATENT DOCUMENTS 4,856,321    8/1989    Smalling et al. .................. 73/40.5

FOREIGN PATENT DOCUMENTS

WO9313414    7/1993    (WO) .................. G01N/29/02

Primary Examiner—Kamini Shah
(74) Attorney, Agent, or Firm—Nutter, McClennen & Fish, LLP

(57) ABSTRACT

An ultrasonic measurement system performs a signal path measurement by directing ultrasonic signals through a gaseous material in a conduit, and processing the detected signals to determine sound speed and to derive the average molecular weight of an unknown hydrocarbon mixture present in the material. The processor includes a plurality of stored tables of critical constants of hydrocarbon mixtures as a function of the average molecular weight of the mixture, and is configured to iteratively set a hypothetical molecular weight, determine the corresponding critical properties, and compute a predicted sound speed. If the two speeds differ, a new weight is set and the procedure is repeated until the predicted sound speed matches the measured speed, indicating that the current estimate is the correct average molecular weight. Once the processor has determined the critical constants from its stored tables, it applies the virial equation of state and mixing rules to determine the predicted sound speed for each hypothetical molecular weight of an unknown mixture of hydrocarbons present, together with one or more known inorganic components, in the fluid material. The processor may be configured for user input of known quantities of one or more gases such as nitrogen, hydrogen, sulfur dioxide, carbon dioxide or other inorganic or non-hydrocarbon gases present in the conduit. Alternatively, all or some of this data may be provided in an automated manner from suitable signals, settings or measurements from upstream conduits, valves or measurement and control instrumentation.

6 Claims, 10 Drawing Sheets

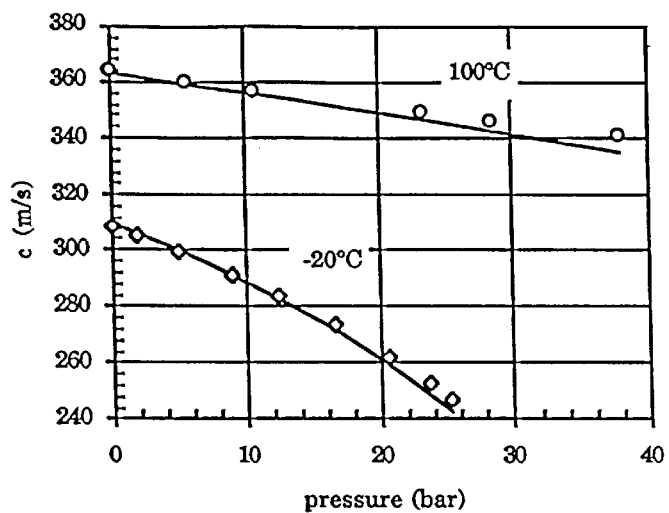
Figure 8
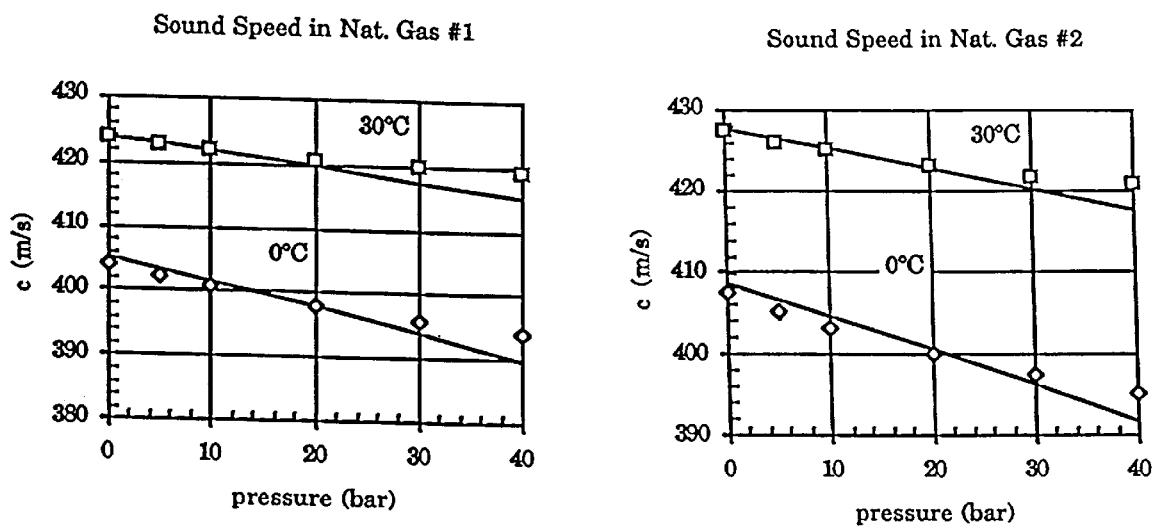
Figure 9A
Figure 9B

ULTRASONIC MEASUREMENT SYSTEM WITH MOLECULAR WEIGHT DETERMINATION

CROSS-REFERENCE TO RELATED APPLICATION

This application is related to U.S. Provisional Patent Application Serial No. 60/101,756, filed Sep. 25, 1998 of which the priority is hereby claimed.

BACKGROUND OF THE INVENTION

The present invention relates to ultrasonic measurement systems, for example systems such as are used to determine properties of a fluid flowing within a conduit. These systems operate by creating an ultrasonic signal burst, and transmitting the burst into the fluid and receiving the signal after it has traveled along a path through the fluid. Two or more related paths may be used (for example upstream and downstream paths, orthogonal paths, or clockwise and counterclockwise paths) to develop signals indicative of sound speed, or of directional differences in sound speed that depend on flow components. Generally the property of the fluid is determined as a function of the transit times of these signals.

Often it is desired to obtain from the signals useful information such as the mass flow rate, or the caloric value of the material flowing in the conduit. In that case further information is necessary and this often requires the system to operate in controlled environments where the user enters extrinsic data via a keyboard to specify the known components of material in the flow so that the signal processor can perform its calculations with the corresponding values of physical parameters for those materials. However, such operation is only possible in a limited number of well controlled circumstances. In some plants, and especially in situations where flue gases are present, the composition of the gas stream will vary over time. It may also be subject to certain fast fluctuations, as occurs in flare gases or certain hydrocarbon processing environments. When the gases present under these measurement conditions are used in bulk processes involving hydrocarbons, the monetary value of material flowing in the conduit can be substantial, and it may be necessary to know its volume and composition with relatively high accuracy for processing, control or environmental reasons.

It would therefore be desirable to extend the useful operating conditions of ultrasonic measurement systems to include flows with varying but unknown composition of hydrocarbon components.

It would also be desirable to provide an ultrasonic measurement system which determines the molecular weight of a component of a fluid flow.

SUMMARY OF THE INVENTION

These and other useful ends are achieved in accordance with a basic embodiment of the invention wherein an ultrasonic transducer propagates a signal through a fluid and determines the average molecular weight of an unknown mixture of hydrocarbons present in the fluid. A processor receives sound speed, pressure and temperature information, and performs an iterative procedure to match a hypothetical composition or average molecular weight to the observed sound speed. In accordance with a preferred aspect of the present invention, the microprocessor stores a number of tables in which the critical pressure, compressibility, acentric factor and heat capacity of hydrocarbon gas have been tabulated as functions of molecular weight. The microprocessor executes a programmed set of calculations for determining the sound speed of a mixture of gases by using the virial equations, determining the virial coefficients from these four properties of the gas.

The processor includes a plurality of stored tables of critical constants of hydrocarbon mixtures as a function of the average molecular weight of the mixture, and is configured to iteratively set a hypothetical molecular weight, determine the corresponding critical properties, and compute a predicted sound speed. If the two speeds differ, a new weight is set and the procedure is repeated until the predicted sound speed matches the measured speed, indicating that the current estimate is the correct average molecular weight. Once the processor has determined the critical constants from its stored tables, it applies the virial equation of state and mixing rules to determine the predicted sound speed for each hypothetical molecular weight of an unknown mixture of hydrocarbons present, together with one or more known inorganic components, in the fluid material. The processor may be configured for user input of known quantities of one or more gases such as nitrogen, hydrogen, sulfur dioxide, carbon dioxide or other inorganic or non-hydrocarbon gases present in the conduit. Alternatively, all or some of this data may be provided in an automated manner from suitable signals, settings or measurements from upstream conduits, valves or measurement and control instrumentation. The hydrocarbon analysis may be used to detect leaky valves or upstream process occurrences, or to evaluate gases in feed loops or outflow conduits.

BRIEF DESCRIPTION OF THE DRAWINGS

These and other features of the invention will be understood from the description herein, taken together with the Figures wherein

FIG. 8 compares sound speed in ethylene as calculated in accordance with the invention, and as measured;

FIGS. 9A and 9B compare calculated and measured sound speed for two natural gases as a function of pressure;

DETAILED DESCRIPTION

The present invention relies upon Applicant's discovery that for a broad class of hydrocarbons, each of the critical physical properties of the gas which are necessary for performing the virial calculations is itself a linear or very well behaved function of the average molecular weight of the mixture. Applicant realized that, by compiling a calibration table for a number of different mixtures spanning the expected range of molecular weights, one can accurately determine all four of the physical constants required for virial calculations from this single value, the average molecular weight. In particular, applicant has found that for common hydrocarbon gases including aromatic, double bonded, and single chain hydrocarbons, the relationship is substantially independent of the particular amounts and types of each chemical structure in the mixture, and depends simply on the average molecular weight. Thus to compile and store reference tables for converting a molecular weight into critical temperature, critical pressure or volume, critical compressibility and acentric factor, it is sufficient to perform these measurements for a large number, e.g., 50–150, of different mixtures of miscellaneous hydrocarbon gases that span the expected range of average molecular weights to be found in the field. Once this is done, gas properties may then be modeled in terms of a single variable, the average molecular weight. By simply changing this single variable and comparing calculated outcomes, a processor may perform an iterative procedure to determine the actual molecular weight, which is a measured of importance in many petrochemical processes.

FIGS. 1–7 show the relationship between average molecular weight of a mixture of hydrocarbon gases with other background gases, and the gas properties of the mixture.

Figure 11:
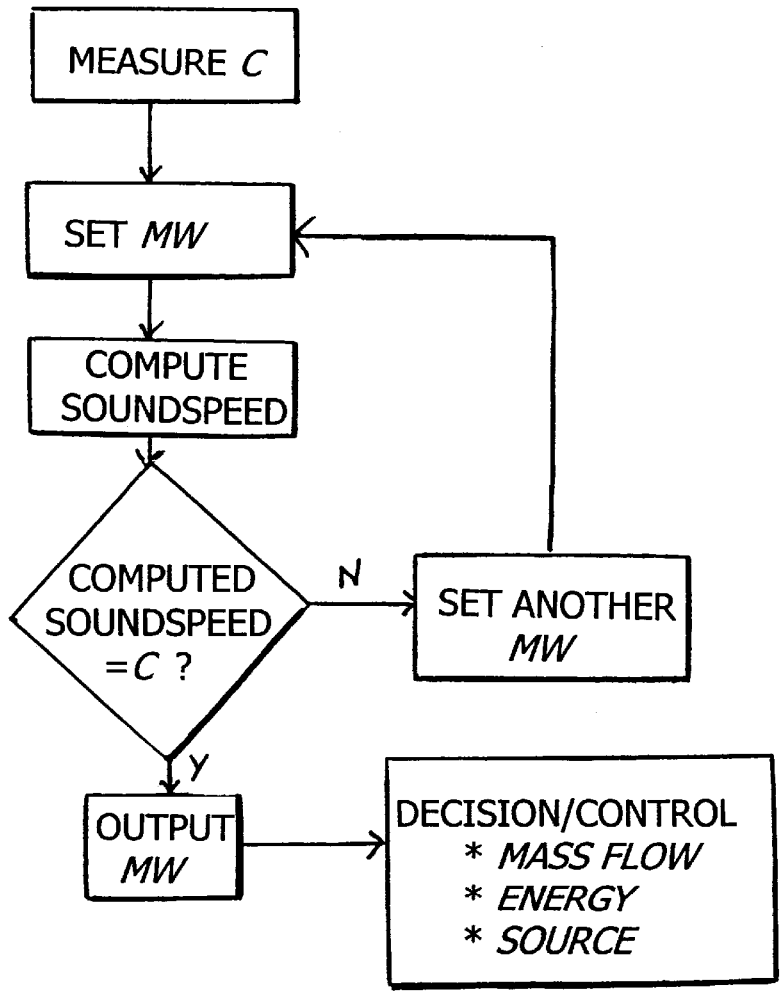
FIG. 11 illustrates operation of the invention.
Figure 12A:
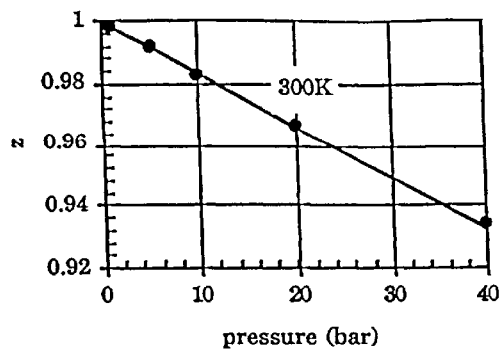
FIG. 12 compares predictive calculations to empirical properties of six gases.
Figure 12B:
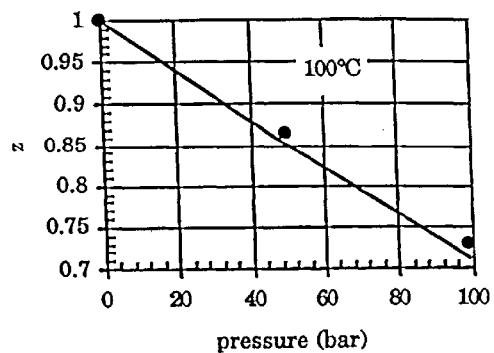
Figure 12C:
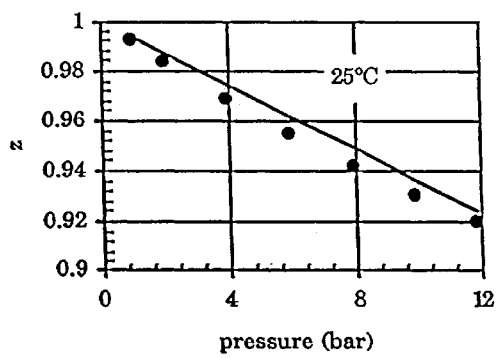
Figure 12D:
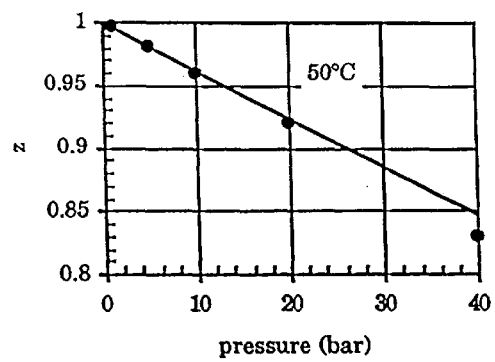
Figure 12E:
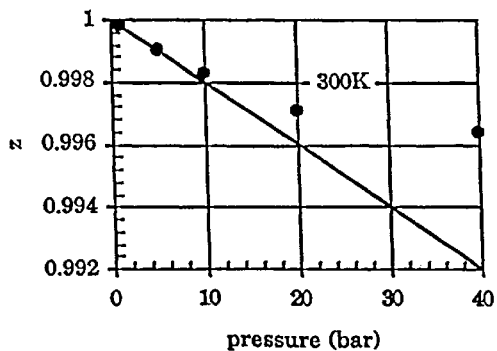
Figure 12F:
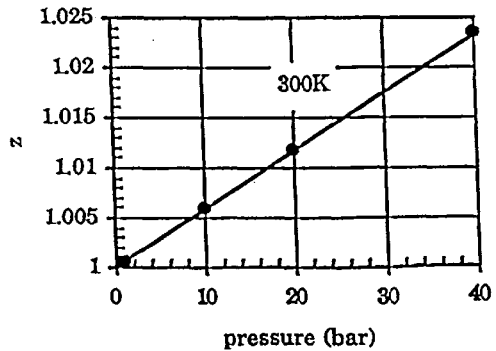

Skipping ahead briefly to FIG. 11, the iterative procedure proceeds as follows. The system is configured for a user to enter the percentage and types of inorganic gases which are present in the mixture such as hydrogen, nitrogen, sulfur dioxide, carbo dioxide and, as needed, any other commonly present inorganic gas. This information may be user-entered, if known, or provided from various sensors and controls, such as pressure and flow transducers or valve setting or control signals from the upstream lines. In the discussion below, it will be assumed that the relevant physical constants for these background gases, all of which have been extensively studied and tabulated in the literature, are stored in the processor, and that if a non-standard background gas is involved, the necessary constants have been determined and stored. The processor then proceeds to estimate the molecular weight of the hydrocarbon component of the fluid stream, and perform a sequence of estimates and calculations to result in a predicted sound speed, which is checked against the measured sound speed. If different, it sets the next molecular weight estimate, and checks its effect on predicted speed, until these converge to the average molecular weight of the hydrogen-carbon components present in the gas.

This is done by first setting the molecular weight low, e.g., equal to that of methane. Using its stored tables the processor determines four values (critical compressibility, acentric factor, and so forth) corresponding to that molecular weight, and using the measured temperature, pressure and sound speed applies the virial coefficient method and mixing rules to determine the predicted sound speed for a hydrocarbon gas with those constants (determined from the set molecular weight) mixed with the amounts of the specified inorganic gases known to be present in the flow, which may, for example, be heuristically known or measured.

The sound speed predicted by the virial equations and mixing rules is then compared to the measured sound speed, and if the results differ, the processor again sets a molecular weight, for example, at the other extreme of the range, e.g., sets mw=130, and again goes through the process of looking up the critical properties corresponding to the tentatively set molecular weight, applying the virial equations to determine an estimated sound speed of the set mixture, and comparing the estimated sound speed with the sound speed actually measured by the transducers. Once the molecular weight has been determined, the output may be used to set desired flow or recirculation based on the caloric value (when used as a combustion feed), or may be used by a decision module or control device to identify the upstream source of one or more components in the flow. This is especially useful to identify aberrations such as stuck or leaky valves giving rise to the presence of an unexpected outflow component.

The microprocessor proceeds in this way, interpolating or extrapolating from successive molecular weight estimates until the set molecular weight yields a theoretical sound speed which matches the observed sound speed. This value is then taken as the average molecular weight of the hydrocarbons present in the flowing material. A more detailed discussion of the relevant virial equations and mixing rules follows, illustrating representative calculations to demonstrate the accuracy achieved by the foregoing method. Because the method employs a fundamental relationship, namely the virial equation of state, and that equation and mixing rules have been well verified, the output of the processor may approach the best accuracy possible for this type of calculation on a complex and unknown mixture.

A representative set of processing steps are discussed below. Background discussions of the virial calculations and the mixing rules for calculating the effects of mixing several gases together may be found in texts and common treaties, for example at chapter 3, section 11, chapter 4 of the Properties of Gases and Liquids, 3rd Ed., R. Reid et al, McGraw-Hill Book Company. Applicant has tabulated the acentric factor, heat capacity at 220° K, 298° K and 560° K temperatures, critical temperature, critical volume and critical compressibility of hydrocarbon mixtures as a function of molecular weight and these tables appear as FIGS. 1–7, respectively, herein. The Figures further show the corresponding values of these properties for hydrogen, nitrogen, carbon dioxide and sulfur dioxide, by way of illustration for inorganic background gases.

Equations for the Virial Method

A. The Virial Equation

The virial equation for sound speed is (J. O. Hirschfelder, C. F. Curtiss, and R. B. Bird *Molecular Theory of Gases and Liquids*, John Wiley and Sons 1964, p. 232)

$$c^2 = \frac{\gamma_o \cdot R \cdot T}{M} \cdot \left[ 1 + \frac{1}{\overline{V}} \cdot \left[ 2 \cdot B + 2 \cdot (\gamma_o - 1) \cdot T \cdot \frac{dB}{dT} + \frac{(\gamma_o - 1)^2}{\gamma_o} \cdot T^2 \cdot \frac{d^2 \cdot B}{dT^2} \right] \right] \quad 1.$$

where $\gamma_o$ is the ideal gas ratio $$\frac{C_P}{C_V},$$

R is the gas constant, T is the temperature, M is the molecular weight, $\overline{V}$ is the molar volume, and B is the second virial coefficient, in units of volume per mole.

The second virial coefficient can be well approximated from critical temperature, critical pressure, and the acentric factor ω (K. S. Pitzer and R. F. Curl, JACS 79, 2369, 1957). The form given below has been modified to fit nonpolar molecules (R. C. Reid, J. M. Prausnitz, and T. K. Sherwood, *The Properties of Gases and Liquids*, McGraw-Hill 1977, pp. 53, 83).

$$B = \frac{R \cdot T_c}{P_c} \cdot \left[ \left[ (.1445 + .0637 \cdot \omega) + -.33 \cdot \frac{T_c}{T} \right] + (-.1385 + .331 \cdot \omega) \cdot \left(\frac{T_c}{T}\right)^2 \ldots + \right.$$
$$\left. (-.0121 - .423 \cdot \omega) \cdot \left(\frac{T_c}{T}\right)^3 + (-.000607 - .008 \cdot \omega) \cdot \left(\frac{T_c}{T}\right)^8 \right]$$

The molar volume $\overline{V}$ is given by $$\overline{V} = \frac{R \cdot T}{P} + B$$

For convenience, the deriviatives of B from the above equation are listed below $$T \cdot \frac{dB}{dT} = \frac{R \cdot T_c}{P_c} \cdot \left[ \begin{array}{c} .33 \cdot \frac{T_c}{T} + (.277 - .662 \cdot \omega) \cdot \left(\frac{T_c}{T}\right)^2 \ldots + \\ (.0363 + 1.269 \cdot \omega) \cdot \left(\frac{T_c}{T}\right)^3 + (.004856 + .064 \cdot \omega) \cdot \left(\frac{T_c}{T}\right)^8 \end{array} \right]$$

$$T^2 \cdot \frac{d^2 \cdot B}{dT^2} = \frac{R \cdot T_c}{P_c} \cdot \left[ \begin{array}{c} -.66 \cdot \frac{T_c}{T} + (-.831 + 1.986 \cdot \omega) \cdot \left(\frac{T_c}{T}\right)^2 \ldots + \\ (-.1452 - 5.076 \cdot \omega) \cdot \left(\frac{T_c}{T}\right)^3 + (-.043704 - .576 \cdot \omega) \cdot \left(\frac{T_c}{T}\right)^8 \end{array} \right]$$

The virial coefficient for mixtures is given by the expression $$B_{mix} = \sum_i \sum_j X_i \cdot X_j \cdot B_{i,j} \quad\quad 3.$$

where $B_{i,j}$ is the virial coefficient for the binary mixture of components i and j, and $B_{i,i}$ is just the virial coefficient of the pure component i. $X_i$ and $X_j$ are mole fractions.

Virial coefficients for binary mixtures can be calculated from the critical constants. But as these are not generally known for mixtures, they must be estimated using mixing rules:

$$T_{c_{i,j}} = \sqrt{T_{c_i} \cdot T_{c_j}} \quad\quad V_{c_{i,j}} = \left[\frac{(V_{c_i})^{\frac{1}{3}} + (V_{c_j})^{\frac{1}{3}}}{2}\right]^3 \quad\quad 4.$$

$$z_{c_{i,j}} = \frac{z_{c_i} + z_{c_j}}{2} \quad\quad \omega_{c_{i,j}} = \frac{\omega_{c_i} + \omega_{c_j}}{2}$$

Note that for single component data $$P_{c_{i,j}} = \frac{z_{c_{i,j}} \cdot R \cdot T_{c_{i,j}}}{V_{c_{i,j}}} \quad\quad V_c = \frac{z_c \cdot R \cdot T_c}{P_c}$$

For example, for a ternary mixture of 1, 2, and 3, the pure component virial coefficients $B_1$, $B_2$, and $B_3$ may be calculated from their critical data, using equation 2. The critical data for the 3 mixture pairs can be estimated from equations 4, and these data can be used to calculate the mixture virial coefficients $B_{12}$, $B_{13}$, and $B_{23}$ from equation 2. These are used in equation 3 to calculate the actual virial coefficient for the mixture. For this example equation 3 becomes $$B_{mix} = X_1^2 \cdot B_1 + X_2^2 \cdot B_2 + X_3^2 \cdot B_3 \ldots + 2 \cdot X_1 \cdot X_2 \cdot B_{12} + 2 \cdot X_1 \cdot X_3 \cdot B_{13} + 2 \cdot X_2 \cdot X_3 \cdot B_{23}$$

where $X_1$, $X_2$, and $X_3$ are the mole fractions of the three components.

B. Method for Determining Molecular Weight

The goal is to obtain molecular weight from sound speed in hydrocarbon gases. The sound speed, temperature, and pressure are known. The concentrations of any non-hydrocarbon species in the mixture are presumed to be known. This is not sufficient information to compute molecular weight using the equations in part A above.

Concentrations, heat capacities, and critical data are missing for the hydrocarbons.

The following scheme is used to estimate the missing data. Correlations are found between molecular weight and heat capacity and critical data for the hydrocarbons. For a presumed value of hydrocarbon molecular weight, these correlations provide values for γ and B and derivatives. An overall virial coefficient is calculated using equation 4, and a sound speed is calculated using equation 1. The calculated sound speed is compared to the observed sound speed, and the calculation is iterated until the value of molecular weight which gives the observed value of sound speed is found.

Iteration is not an instructive approach for this Mathcad document. Instead, the sound speed will be found using the virial equation for the known case of 85% methane in nitrogen. Then the virial method will be applied to determine what molecular weight gives the same sound speed, for the unknown case of 85% unspecified hydrocarbon(s) in nitrogen.

Let $X_H$:=0.85 be the hydrocarbon concentration, $X_B$:= 0.85 be the methane concentration, and $X_A$:=0.15 be the nitrogen concentration The unknown molecular weight will be found to be mH=0.0159 kg/mole.

The temperature is T:=298.15 kelvins, and the pressure is P:=20 atmospheres.

1. Coefficients

The correlation for heat capacity is determined using a weighted quadratic fit. The results are given in terms of absolute temperature T and the molecular weight mH (kg/mole) of the hydrocarbons. Cv is in units of joules per mole, with $R_{gas}$=8.31441 joules*mole$^{-1}$*K$^{-1}$.

$R_{gas}$:=8.31441

The hydrocarbon heat capacity coefficients are $a_{00} := 1.8414 \quad a_{01} := 1.5765 \cdot 10^{-3} \quad a_{02} := -1.5128 \cdot 10^{-6}$ $a_{10} := -30.348 \quad a_{11} := 0.32274 \quad a_{12} := -2.4852 \cdot 10^{-5}$ $a_{20} := -682.06 \quad a_{21} := 6.7565 \quad a_{22} := -5.7596 \cdot 10^{-3}$ Ideal gas heat capacity $C_v1$ for the hydrocarbons is given by $$C_{vH} := R_{gas} \cdot \begin{bmatrix} (a_{00} + a_{01} \cdot T + a_{02} \cdot T^2) \ldots + \\ (a_{10} + a_{11} \cdot T + a_{12} \cdot T^2) \cdot mH \ldots + \\ (a_{20} + a_{21} \cdot T + a_{22} \cdot T^2) \cdot mH^2 \end{bmatrix}$$

in units of $R_{gas}$

The other hydrocarbon data are the critical temperature $T_c$ (K), critical volume $V_c$ (cc/mole), critical compressibility $z_c$, and acentric factor $\omega$. These are independent of temperature. Coefficients were determined from least square fits.

$b_0 := 24.979 \quad b_1 := 12581 \quad b_2 := -115362 \quad b_3 := 413791$ $c_0 := 41.053 \quad c_1 := 3080.8 \quad c_2 := 6081.2$ $d_0 := .28566 \quad d_1 := -.19443$ $e_0 := 3.114 \cdot 10^{-2} \quad e_1 := 2.6938$ The values are calculated from the following (mH in units of kg/mole)

$T_{cH} := b_0 + b_1 \cdot mH + b_2 \cdot mH^2 + b_3 \cdot mH^3$
$V_{cH} := c_0 + c_1 \cdot mH + c_2 \cdot mH^2$
$z_{cH} := d_0 + d_1 \cdot mH$
$\omega_H := e_0 + e_1 \cdot mH$ Data for non-hydrocarbon gases are given directly. For example, for nitrogen (let nitrogen be gas A)

$m_A := 0.028013 \quad T_{cA} := 126.2 \quad V_{cA} := 89.645$ $\omega_A := 0.04 \quad z_{cA} := 0.29 \quad a_{0A} := 7.44$ $a_{1A} := -3.24 \cdot 10^{-3} \quad a_{2A} := 6.4 \cdot 10^{-6} \quad a_{3A} := -2.79 \cdot 10^{-9}$ The coefficients for heat capacity are given as they are usually found, for $C_p$ in units of $cal \cdot mole^{-1} \cdot K^{-1}$. For our units $C_{vA} := 4.184 \cdot (a_{0A} + a_{1A} \cdot T + a_{2A} \cdot T^2 + a_{3A} \cdot T^3) - R_{gas}$ using the conversion factor 4.184 joule/cal.

For purposes of demonstration only, let gas B be methane.

$m_B := 0.016043 \quad T_{cB} := 190.6 \quad V_{cB} := 99.214$ $\omega_B := 0.008 \quad z_{cB} := 0.288 \quad a_{0B} := 4.598$ $a_{1B} := 1.245 \cdot 10^{-2} \quad a_{2B} := 2.86 \cdot 10^{-6} \quad a_{3B} := -2.703 \cdot 10^{-9}$ $C_{vB} := 4.184 \cdot (a_{0B} + a_{1B} \cdot T + a_{2B} \cdot T^2 + a_{3B} \cdot T^3) - R_{gas}$ It is expected that similar coefficients will be programmed for a number of other inorganic gases.

It is convenient to tabulate the coefficients of equation 2.

$f_0 := 0.1445 \quad g_0 := 6.37 \cdot 10^{-2}$ $f_1 := -0.33 \quad g_1 := 0$ $f_2 := -0.1385 \quad g_2 := 0.331$ $f_3 := -1.21 \cdot 10^{-2} \quad g_3 := -0.423$ $f_4 := -6.07 \cdot 10^{-4} \quad g_4 := -8 \cdot 10^{-3}$

2. Mixture properties

Consider mixtures of hydrocarbons with known amounts of nitrogen and hydrogen sulfide. The mixture properties are given by $T_{cAH} := \sqrt{T_{cA} \cdot T_{cH}} \quad V_{cAH} := \frac{1}{8} \cdot \left(V_{cA}^{\frac{1}{3}} + V_{cH}^{\frac{1}{3}}\right)^3$ $T_{cBH} := \sqrt{T_{cB} \cdot T_{cH}} \quad V_{cBH} := \frac{1}{8} \cdot \left(V_{cB}^{\frac{1}{3}} + V_{cH}^{\frac{1}{3}}\right)^3$ $T_{cAB} := \sqrt{T_{cA} \cdot T_{cB}} \quad V_{cAB} := \frac{1}{8} \cdot \left(V_{cA}^{\frac{1}{3}} + V_{cB}^{\frac{1}{3}}\right)^3$ $z_{cAH} := \frac{1}{2} \cdot (z_{cA} + z_{cH}) \quad \omega_{AH} := \frac{1}{2} \cdot (\omega_A + \omega_H)$ $z_{cBH} := \frac{1}{2} \cdot (z_{cB} + z_{cH}) \quad \omega_{BH} := \frac{1}{2} \cdot (\omega_B + \omega_H)$ $z_{cAB} := \frac{1}{2} \cdot (z_{cA} + z_{cB}) \quad \omega_{AB} := \frac{1}{2} \cdot (\omega_A + \omega_B)$

3. Virial Coefficients and derivatives

Let $$B1 = T \cdot \frac{dB}{dT} \quad B2 = T^2 \cdot \frac{d^2 \cdot B}{dT^2}$$

The virial coefficients for the unknown hydrocarbon mixture are given by (units of cc/mole)

$$B_H := \frac{V_{cH}}{z_{cH}} \cdot \begin{bmatrix} (f_0 + g_0 \cdot \omega_H) + f_1 \cdot \left(\frac{T_{cH}}{T}\right) + (f_2 + g_2 \cdot \omega_H) \cdot \left(\frac{T_{cH}}{T}\right)^2 \ldots + \\ (f_3 + g_3 \cdot \omega_H) \cdot \left(\frac{T_{cH}}{T}\right)^3 + (f_4 + g_4 \cdot \omega_H) \cdot \left(\frac{T_{cH}}{T}\right)^8 \end{bmatrix}$$

$$B1_H := \frac{V_{cH}}{z_{cH}} \cdot \begin{bmatrix} -f_1 \cdot \frac{T_{cH}}{T} + -2 \cdot (f_2 + g_2 \cdot \omega_H) \cdot \left(\frac{T_{cH}}{T}\right)^2 \ldots + \\ -3 \cdot (f_3 + g_3 \cdot \omega_H) \cdot \left(\frac{T_{cH}}{T}\right)^3 + -8 \cdot (f_4 + g_4 \cdot \omega_H) \cdot \left(\frac{T_{cH}}{T}\right)^8 \end{bmatrix}$$

$$B2_H := \frac{V_{cH}}{z_{cH}} \cdot \begin{bmatrix} 2 \cdot f_1 \cdot \left(\frac{T_{cH}}{T}\right) + 6 \cdot (f_2 + g_2 \cdot \omega_H) \cdot \left(\frac{T_{cH}}{T}\right)^2 \ldots + \\ 12 \cdot (f_3 + g_3 \cdot \omega_H) \cdot \left(\frac{T_{cH}}{T}\right)^3 + 72 \cdot (f_4 + g_4 \cdot \omega_H) \cdot \left(\frac{T_{cH}}{T}\right)^8 \end{bmatrix}$$

The virial coefficients for pure nitrogen are $$B_A := \frac{V_{cA}}{z_{cA}} \cdot \begin{bmatrix} (f_0 + g_0 \cdot \omega_A) + f_1 \cdot \left(\frac{T_{cA}}{T}\right) + (f_2 + g_2 \cdot \omega_A) \cdot \left(\frac{T_{cA}}{T}\right)^2 \ldots + \\ (f_3 + g_3 \cdot \omega_A) \cdot \left(\frac{T_{cA}}{T}\right)^3 + (f_4 + g_4 \cdot \omega_A) \cdot \left(\frac{T_{cA}}{T}\right)^8 \end{bmatrix}$$

$$B1_A := \frac{V_{cA}}{z_{cA}} \cdot \left[ \begin{array}{l} -f_1 \cdot \frac{T_{cA}}{T} + -2 \cdot (f_2 + g_2 \cdot \omega_A) \cdot \left(\frac{T_{cA}}{T}\right)^2 \cdots + \\ -3 \cdot (f_3 + g_3 \cdot \omega_A) \cdot \left(\frac{T_{cA}}{T}\right)^3 + -8 \cdot (f_4 + g_4 \cdot \omega_A) \cdot \left(\frac{T_{cA}}{T}\right)^8 \end{array} \right]$$

$$B2_A := \frac{V_{cA}}{z_{cA}} \cdot \left[ \begin{array}{l} 2 \cdot f_1 \cdot \left(\frac{T_{cA}}{T}\right) + 6 \cdot (f_2 + g_2 \cdot \omega_A) \cdot \left(\frac{T_{cA}}{T}\right)^2 \cdots + \\ 12 \cdot (f_3 + g_3 \cdot \omega_A) \cdot \left(\frac{T_{cA}}{T}\right)^3 + 72 \cdot (f_4 + g_4 \cdot \omega_H) \cdot \left(\frac{T_{cH}}{T}\right)^8 \end{array} \right]$$

The virial coefficients for pure methane are $$B_B := \frac{V_{cB}}{z_{cB}} \cdot \left[ \begin{array}{l} (f_0 + g_0 \cdot \omega_B) + f_1 \cdot \left(\frac{T_{cB}}{T}\right) + (f_2 + g_2 \cdot \omega_B) \cdot \left(\frac{T_{cB}}{T}\right)^2 \cdots + \\ (f_3 + g_3 \cdot \omega_B) \cdot \left(\frac{T_{cB}}{T}\right)^3 + (f_4 + g_4 \cdot \omega_B) \cdot \left(\frac{T_{cB}}{T}\right)^8 \end{array} \right]$$

$$B1_B := \frac{V_{cB}}{z_{cB}} \cdot \left[ \begin{array}{l} -f_1 \cdot \frac{T_{cB}}{T} + -2 \cdot (f_2 + g_2 \cdot \omega_B) \cdot \left(\frac{T_{cB}}{T}\right)^2 \cdots + \\ -3 \cdot (f_3 + g_3 \cdot \omega_B) \cdot \left(\frac{T_{cB}}{T}\right)^3 + -8 \cdot (f_4 + g_4 \cdot \omega_B) \cdot \left(\frac{T_{cB}}{T}\right)^8 \end{array} \right]$$

$$B2_B := \frac{V_{cB}}{z_{cB}} \cdot \left[ \begin{array}{l} 2 \cdot f_1 \cdot \left(\frac{T_{cB}}{T}\right) + 6 \cdot (f_2 + g_2 \cdot \omega_B) \cdot \left(\frac{T_{cB}}{T}\right)^2 \cdots + \\ 12 \cdot (f_3 + g_3 \cdot \omega_B) \cdot \left(\frac{T_{cB}}{T}\right)^3 + 72 \cdot (f_4 + g_4 \cdot \omega_B) \cdot \left(\frac{T_{cB}}{T}\right)^8 \end{array} \right]$$

The virial coefficients for the nitrogen-hydrocarbon mix are $$B_{AH} := \frac{V_{cAH}}{z_{cAH}} \cdot \left[ \begin{array}{l} (f_0 + g_0 \cdot \omega_{AH}) + f_1 \cdot \left(\frac{T_{cAH}}{T}\right) + (f_2 + g_2 \cdot \omega_{AH}) \cdot \left(\frac{T_{cAH}}{T}\right)^2 \cdots + \\ (f_3 + g_3 \cdot \omega_{AH}) \cdot \left(\frac{T_{cAH}}{T}\right)^3 + (f_4 + g_4 \cdot \omega_{AH}) \cdot \left(\frac{T_{cAH}}{T}\right)^8 \end{array} \right]$$

$$B1_{AH} := \frac{V_{cAH}}{z_{cAH}} \cdot \left[ \begin{array}{l} -f_1 \cdot \left(\frac{T_{cAH}}{T}\right) + -2 \cdot (f_2 + g_2 \cdot \omega_{AH}) \cdot \left(\frac{T_{cAH}}{T}\right)^2 \cdots + \\ -3 \cdot (f_3 + g_3 \cdot \omega_{AH}) \cdot \left(\frac{T_{cAH}}{T}\right)^3 + -8 \cdot (f_4 + g_4 \cdot \omega_{AH}) \cdot \left(\frac{T_{cAH}}{T}\right)^8 \end{array} \right]$$

$$B2_{AH} := \frac{V_{cAH}}{z_{cAH}} \cdot \left[ \begin{array}{l} 2 \cdot f_1 \cdot \left(\frac{T_{cAH}}{T}\right) + 6 \cdot (f_2 + g_2 \cdot \omega_{AH}) \cdot \left(\frac{T_{cAH}}{T}\right)^2 \cdots + \\ 12 \cdot (f_3 + g_3 \cdot \omega_{AH}) \cdot \left(\frac{T_{cAH}}{T}\right)^3 + 72 \cdot (f_4 + g_4 \cdot \omega_{AH}) \cdot \left(\frac{T_{cAH}}{T}\right)^8 \end{array} \right]$$

The virial coefficients for the nitrogen-methane mix are $$B_{AB} := \frac{V_{cAB}}{z_{cAB}} \cdot \left[ \begin{array}{l} (f_0 + g_0 \cdot \omega_{AB}) + f_1 \cdot \left(\frac{T_{cAB}}{T}\right) + (f_2 + g_2 \cdot \omega_{AB}) \cdot \left(\frac{T_{cAB}}{T}\right)^2 \cdots + \\ (f_3 + g_3 \cdot \omega_{AB}) \cdot \left(\frac{T_{cAB}}{T}\right)^3 + (f_4 + g_4 \cdot \omega_{AB}) \cdot \left(\frac{T_{cAB}}{T}\right)^8 \end{array} \right]$$

$$B1_{AB} := \frac{V_{cAB}}{z_{cAB}} \cdot \left[ \begin{array}{l} -f_1 \cdot \left(\frac{T_{cAB}}{T}\right) + -2 \cdot (f_2 + g_2 \cdot \omega_{AB}) \cdot \left(\frac{T_{cAB}}{T}\right)^2 \cdots + \\ -3 \cdot (f_3 + g_3 \cdot \omega_{AB}) \cdot \left(\frac{T_{cAB}}{T}\right)^3 + -8 \cdot (f_4 + g_4 \cdot \omega_{AB}) \cdot \left(\frac{T_{cAB}}{T}\right)^8 \end{array} \right]$$

$$B2_{AB} := \frac{V_{cAB}}{z_{cAB}} \cdot \left[ \begin{array}{l} 2 \cdot f_1 \cdot \left(\frac{T_{cAB}}{T}\right) + 6 \cdot (f_2 + g_2 \cdot \omega_{AB}) \cdot \left(\frac{T_{cAB}}{T}\right)^2 \cdots + \\ 12 \cdot (f_3 + g_3 \cdot \omega_{AB}) \cdot \left(\frac{T_{cAB}}{T}\right)^3 + 72 \cdot (f_4 + g_4 \cdot \omega_{AB}) \cdot \left(\frac{T_{cAB}}{T}\right)^8 \end{array} \right]$$

The overall virial coefficients for the unknown hydrocarbon are $$Bx := B_H \cdot X_H^2 + B_A \cdot X_A^2 + 2 \cdot B_{AH} \cdot X_H \cdot X_A$$

$$Bx1 := B1_H \cdot X_H^2 + B1_A \cdot X_A^2 + 2 \cdot B1_{AH} \cdot X_H \cdot X_A$$

$$Bx2 := B2_H \cdot X_H^2 + B2_A \cdot X_A^2 + 2 \cdot B2_{AH} \cdot X_H \cdot X_A$$

and the overall virial coefficients for the known mixture are $$B := B_B \cdot X_B^2 + B_A \cdot X_A^2 + 2 \cdot B_{AB} \cdot X_A \cdot X_B$$

$$B1 := B1_B \cdot X_B^2 + B1_A \cdot X_A^2 + 2 \cdot B1_{AB} \cdot X_A \cdot X_B$$

$$B2 := B2_B \cdot X_B^2 + B2_A \cdot X_A^2 + 2 \cdot B2_{AB} \cdot X_A \cdot X_B$$

The overall molecular weights, unknown and known, are $$mx := mH \cdot X_H + m_A \cdot X_A$$

$$m := m_B \cdot X_B + m_A \cdot X_A$$

The gammas are $$C_{vx} := \frac{C_{vH}}{R_{gas}} \cdot X_H + \frac{C_{vA}}{R_{gas}} \cdot X_A \qquad \gamma_x := \frac{C_{vx} + 1}{C_{vx}}$$

$$C_v := \frac{C_{vB}}{R_{gas}} \cdot X_B + \frac{C_{vA}}{R_{gas}} \cdot X_A \qquad \gamma := \frac{C_v + 1}{C_v}$$

The molar volumes are $$Vx := \frac{R_{gas} \cdot T}{0.101325 \cdot P} + Bx \qquad V := \frac{R_{gas} \cdot T}{0.101325 \cdot P} + B$$

$$c := \sqrt{\frac{\gamma \cdot R_{gas} \cdot T}{m} \cdot \left[ 1 + \frac{1}{V} \cdot \left[ 2 \cdot B + 2 \cdot (\gamma - 1) \cdot B1 + \frac{(\gamma - 1)^2}{\gamma} \cdot B2 \right] \right]}$$

$$cx = 423.0542 \qquad c = 423.0542$$

where 0.101325 is the conversion of cc*atm to Pa*m^3

Finally, cx is the uiknown hydrocarbon sound speed, which is a function of mH, and c is the sound speed of the known mixture.

$$cx := \sqrt{\frac{\gamma_x \cdot R_{gas} \cdot T}{mx} \cdot \left[ 1 + \frac{1}{Vx} \cdot \left[ 2 \cdot Bx + 2 \cdot (\gamma_x - 1) \cdot Bx1 + \frac{(\gamma_x - 1)^2}{\gamma_x} \cdot Bx2 \right] \right]}$$

-continued $$c := \sqrt{\frac{\gamma \cdot R_{gas} \cdot T}{m} \cdot \left[1 + \frac{1}{V} \cdot \left[2 \cdot B + 2 \cdot (\gamma - 1) \cdot B1 + \frac{(\gamma - 1)^2}{\gamma} \cdot B2\right]\right]}$$

$$cx = 423.0542 \qquad c = 423.0542$$

We choose the value mH=0.01587314 to make c=cx. The unknown molecular weight is mx=0.0176941 and the actual molecular weight is m=0.0178385 for an error of $$\frac{mx - m}{m} = -0.81 \cdot \%$$

The compressibility is $$z := 1 + \frac{Bx \cdot 0.101325 \cdot P}{R_{gas} \cdot T} \quad \text{with a value of} \quad z = 0.9704$$

The foregoing equations thus allow the determination of sound speed from molecular weight, and provide all the necessary relationships for eliminating or determining any unknowns if the temperature and pressure are known. The calculations are readily automated. By way of example, attached hereto as Appendix I, is a computer program which implements an iterative molecular weight determination as described above. The program is written in BASIC.

In a prototype operating embodiment, the processor is adapted to receive input data specifying the temperature, pressure and percentage of each of the above four standard inorganic gases, and to then calculate the speed of sound resulting from a mixture of these inorganic gases with a hydrocarbon mixture having an unknown average molecular weight. The processor follows the iteration procedure described above to estimate the actual average molecular weight using the foregoing empirical relationships and mixing rules under programmed control. This iteration procedure yields a value of the molecular weight which, if assumed for the hydrocarbon portion of the fluid in the conduit, accurately predicts the measured speed of sound. Discussion of representative calculations follows.

DISCUSSION AND EXAMPLES

The molecular weight of an unknown combination of hydrocarbon gases in calculated from the speed of sound in the gas mixture. Applicant found this to be possible for a homologous series, such as the hydrocarbon gases, because the gas properties which influence the speed of sound are also approximate functions of molecular weight. The virial equation of state is used to calculate the speed of sound in a gas under non-ideal conditions. For intermediate pressures (up to 20–50 bars), only the second virial coefficient is needed. This is estimated from the gas critical data. In addition, data on molecular weight, heat capacity, temperature, and pressure are used.

The virial equation for sound speed in a pure substance is illustrated by comparing the calculated (solid lines) and measured (open circles and diamonds) speed of sound ethylene. This data is summarized in Table I, and is graphically plotted in FIG. 8.

TABLE I

Sound Speed in Ethylene

| −20° C. pressure (bar) | calculated (virial eqn.) m/s | measured (1) m/s |
|---|---|---|
| 0.00 | 309.50 | 308.46 |
| 1.89 | 306.00 | 305.06 |
| 4.91 | 300.08 | 299.42 |
| 9.01 | 291.23 | 291.29 |
| 12.46 | 282.94 | 283.58 |
| 16.53 | 271.97 | 273.45 |
| 20.60 | 259.40 | 262.26 |
| 23.55 | 249.10 | 253.08 |
| 25.22 | 242.72 | 246.75 |
| 100° C. | | |
| 0.00 | 363.16 | 363.77 |
| 5.73 | 359.42 | 360.21 |
| 10.74 | 356.02 | 357.08 |
| 23.24 | 346.94 | 349.42 |
| 28.54 | 342.80 | 346.28 |
| 37.94 | 335.00 | 341.01 |

The virial equation for the speed of sound in mixtures of known composition is illustrated by comparing the calculated (solid lines) and measured (open circles and diamonds) speed of sound in two different natural gases, shown in Chart II and Chart III of FIGS. 9A and 9B, respectively. The corresponding data points are tabulated in TABLE II and TABLE III, respectively. As seen in these examples, the measured speed of sound begins to deviate from the calculated speed of sound as pressure increases above about 20 bar.

TABLE II

| Natural Gas 1 composition | | Press. (bar) ° C. | calc. (virial) m/s | meas. (2) m/s |
|---|---|---|---|---|
| C1 | 81.20% | 0.01 | 405.14 | 404.10 |
| C2 | 1.05% | 5 | 403.41 | 402.40 |
| C3 | 0.04% | 10 | 401.62 | 400.90 |
| C4+ | 0.04% | 20 | 397.90 | 398.10 |
| CO2 | 0.49% | 30 | 393.99 | 395.80 |
| N2 | 17.17% | 40 | 389.85 | 394.10 |
| | | 30° C. | | |
| | | 0.01 | 423.98 | 423.70 |
| | | 5 | 422.95 | 422.90 |
| | | 10 | 421.90 | 422.10 |
| | | 20 | 419.75 | 420.70 |
| | | 30 | 417.53 | 419.70 |
| | | 40 | 415.23 | 419.10 |

TABLE III

| Natural Gas 2 composition | | Press. (bar) ° C. | calc. (virial) m/s | meas. (2) m/s |
|---|---|---|---|---|
| C1 | 84.50% | 0.01 | 408.73 | 407.50 |
| C2 | 1.46% | 5 | 406.81 | 405.40 |
| C3 | 3.47% | 10 | 404.84 | 403.40 |
| C4+ | 0.06% | 20 | 400.72 | 400.10 |
| CO2 | 0.59% | 30 | 396.36 | 397.40 |
| N2 | 13.34% | 40 | 391.75 | 395.30 |
| | | 30° C. | | |
| | | 0.01 | 427.63 | 427.40 |
| | | 5 | 426.46 | 426.00 |

TABLE III-continued

| Natural Gas 2 composition | Press. (bar) ° C. | calc. (virial) m/s | meas. (2) m/s |
|---|---|---|---|
| | 10 | 425.26 | 424.90 |
| | 20 | 422.80 | 423.00 |
| | 30 | 420.25 | 421.70 |
| | 40 | 417.61 | 420.80 |

As noted above, using the relationship between molecular weight and each of the critical properties, and heat capacity, applicant is able to calculate the average molecular weight when onle the temperature, pressure and speed of sound are measured.

The method may be summarized as follows. All the hydrocarbon gases are considered to be a single component with an (arbitrarily assigned) molecular weight. A sound speed measurment is made. By using the virial equation and the correlations of gas properties with molecular weight, a theoretical value for the speed of sound is also calculated. The calculated value is compared to the observed speed of sound, and if different, a new molecular weight value is chosen, and the calculations repeated. This process is iterated until a molecular weight is found which gives a calculated speed of sound equal to the observed speed of sound. Known amounts of inorganic components are considered as additional components of the mixture and are accounted for by using the mixing rules as above for virial coefficients.

This virial method covers a temperature range of about −50° C. to 300° C. and a molecular weight range of about 2 to 130 g/mole. A pressure range cannot be explicitly given, and will depend to some degree upon the particular gases involved. The method appears to produce satisfactory results at pressures up to 20 bars in all cases tested so far.

RESULTS FOR MOLECULAR WEIGHT CALCULATIONS

Figure 1:
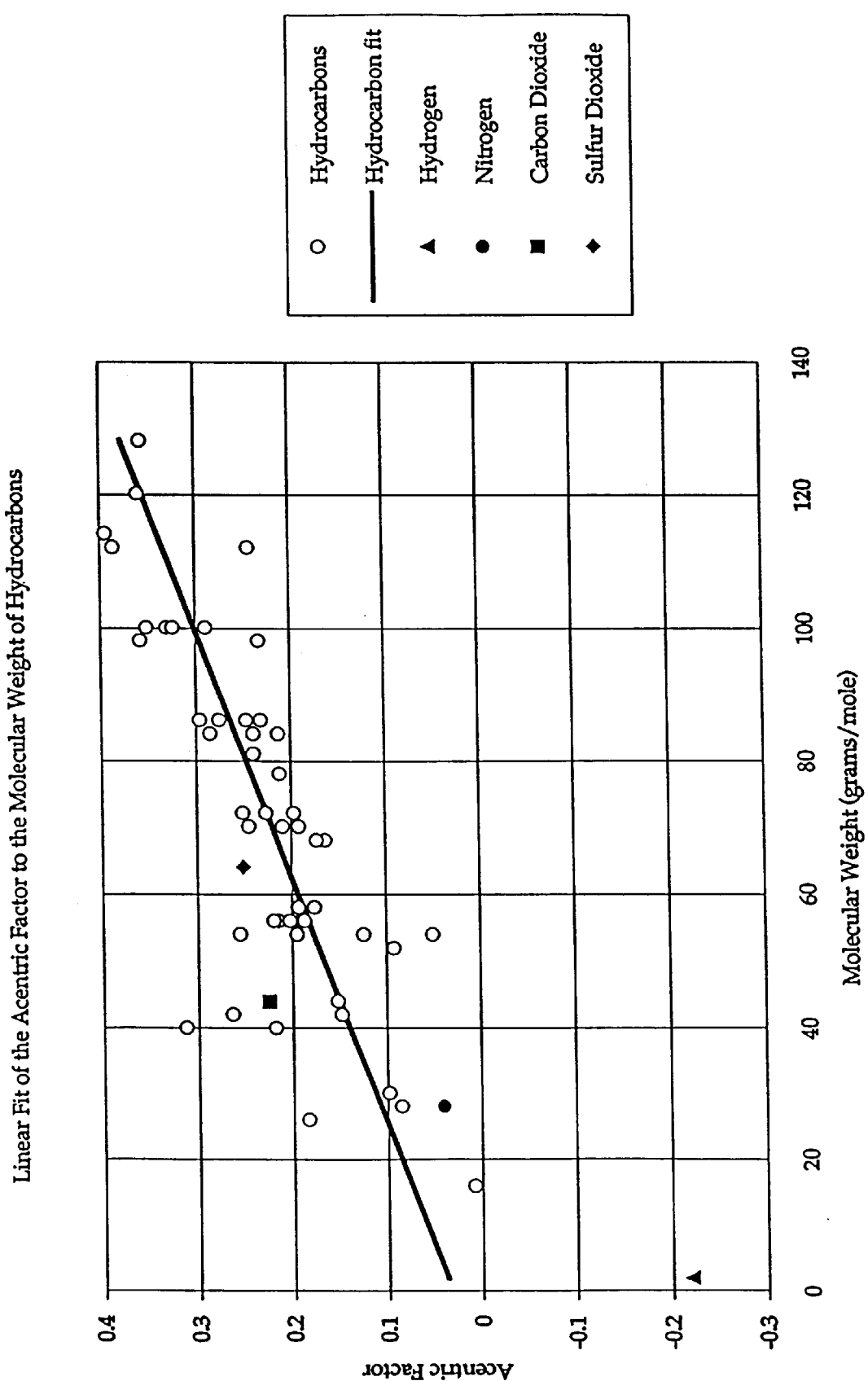
FIG. 1 illustrates a relationship between molecular weight of hydrocarbons and acentric factor.
Figure 2:
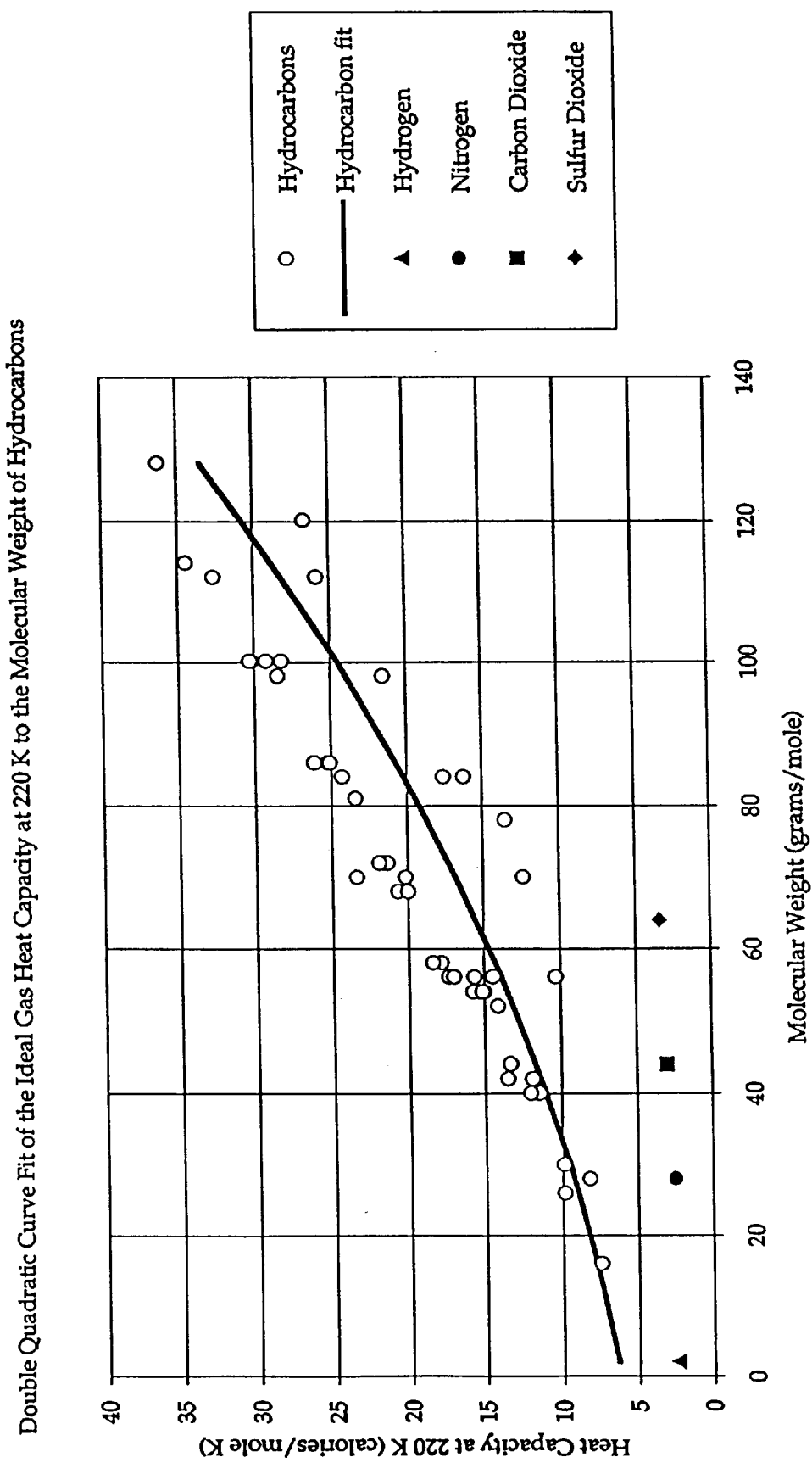
FIG. 2 illustrates a relationship between molecular weight of hydrocarbons and ideal gas heat capacity at 220° K.
Figure 3:
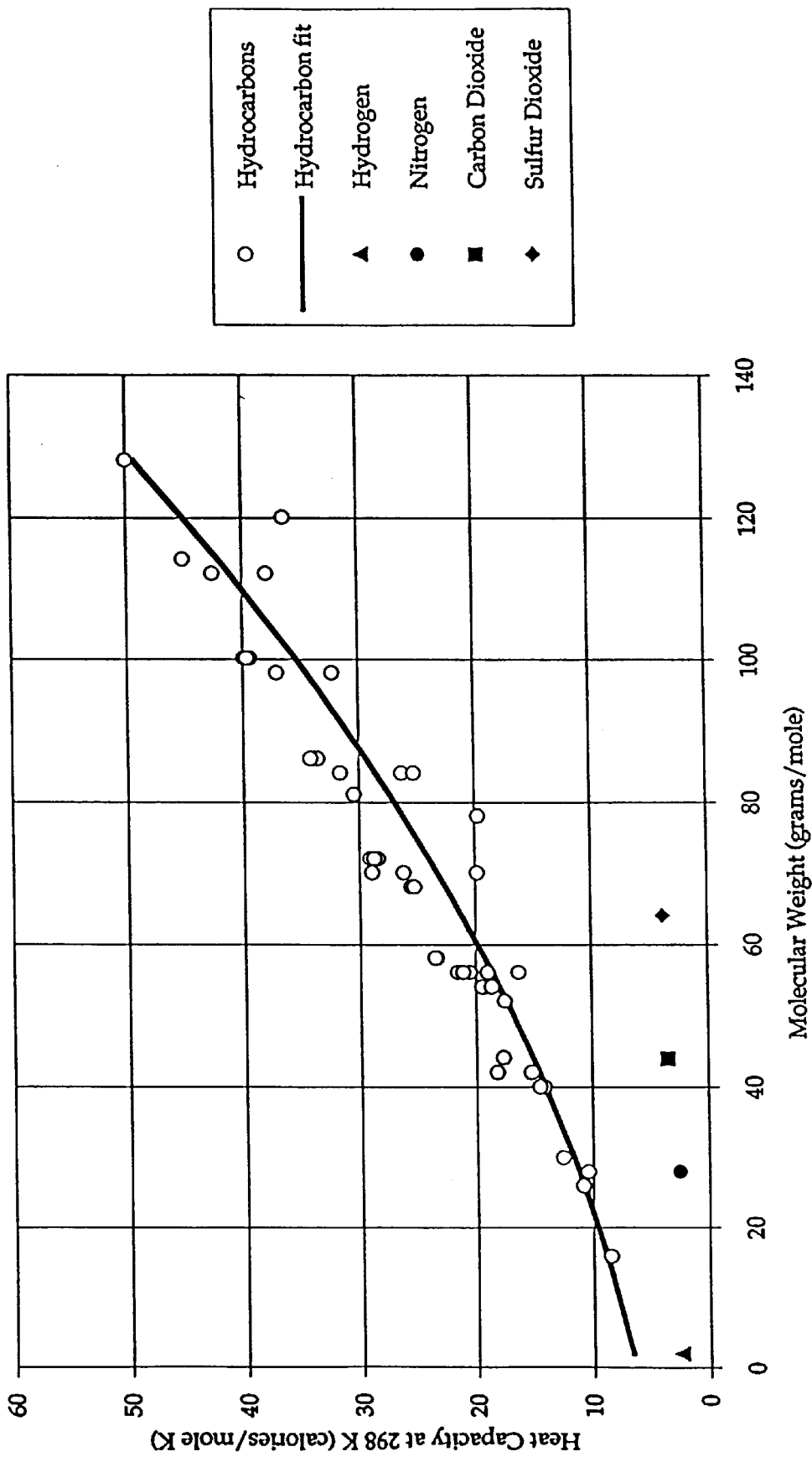
FIG. 3 illustrates a relationship between molecular weight of hydrocarbons and ideal gas heat capacity at 298° K.
Figure 4:
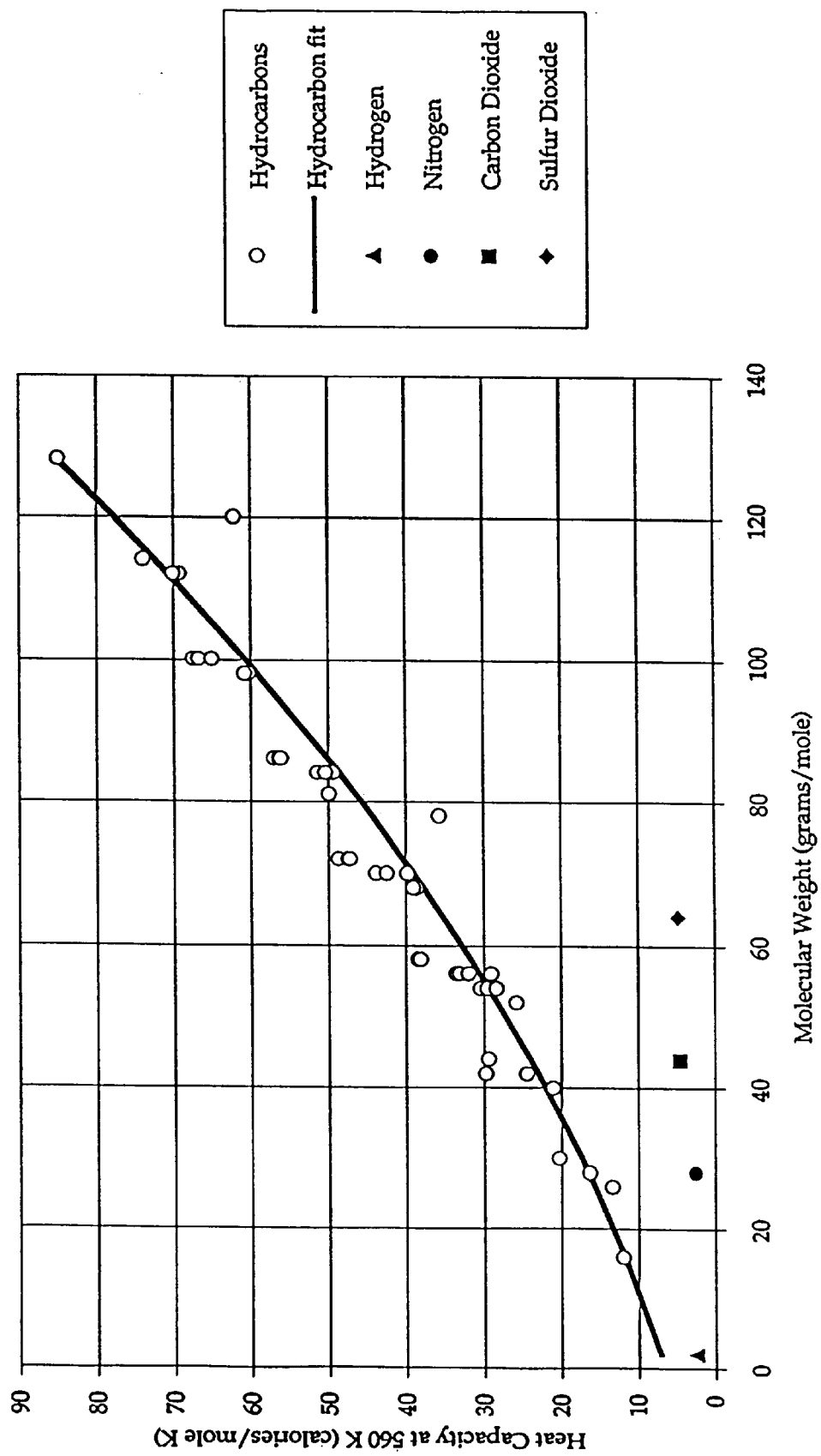
FIG. 4 illustrates a relationship between molecular weight of hydrocarbons and ideal gas heat capacity at 560° K.
Figure 5:
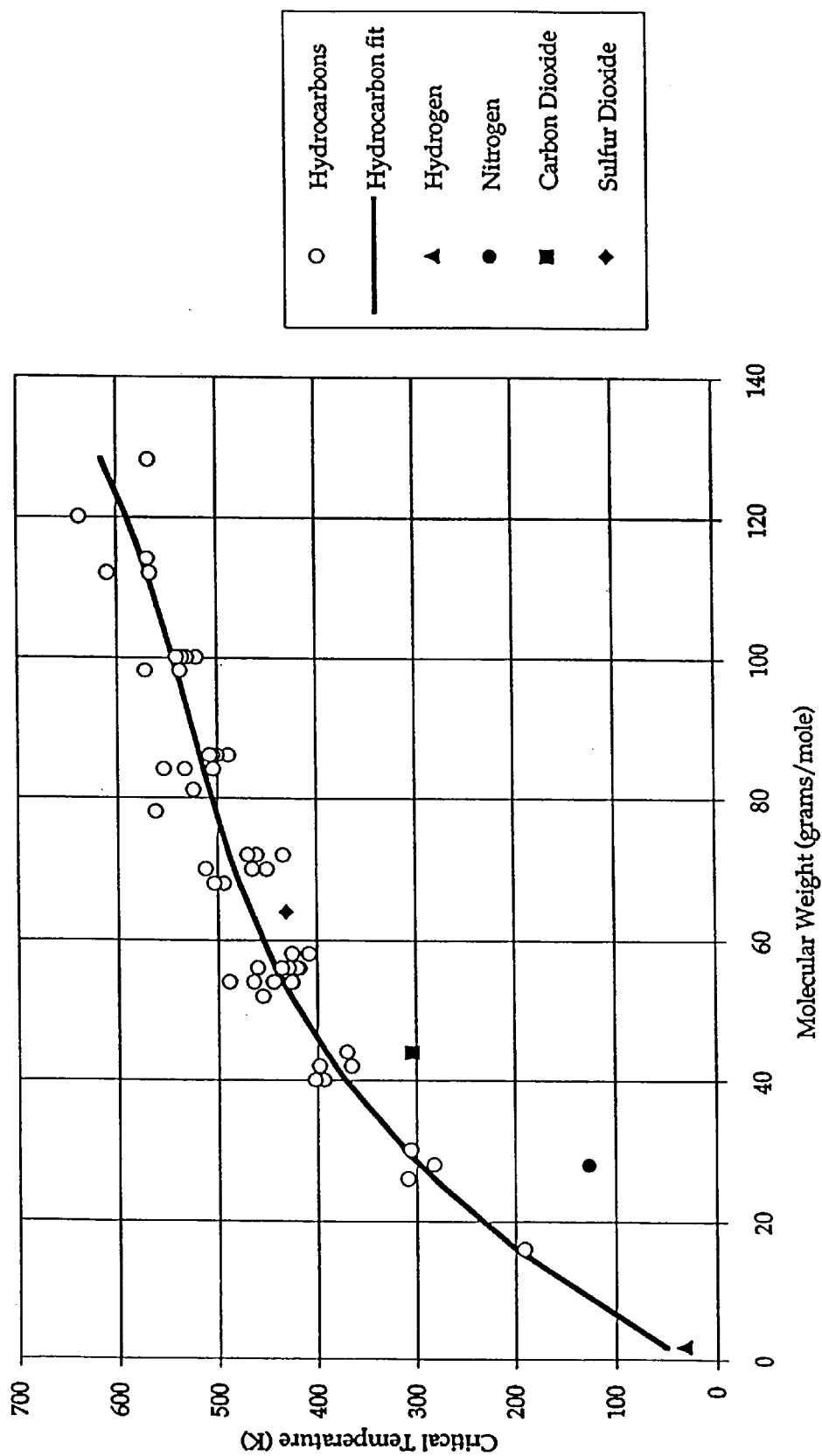
FIG. 5 illustrates a relationship between molecular weight of hydrocarbons and critical temperature.
Figure 6:
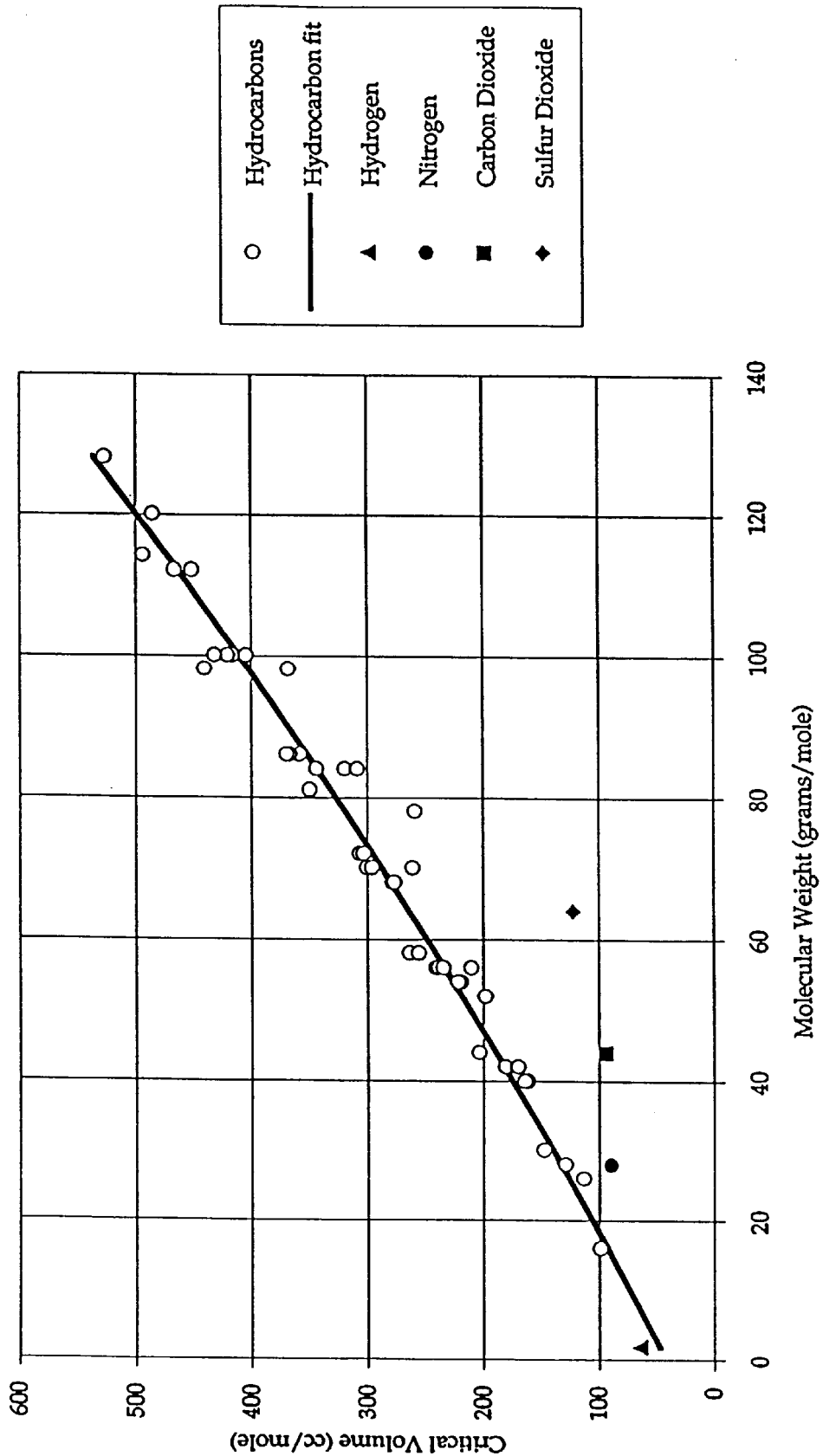
FIG. 6 illustrates a relationship between molecular weight of hydrocarbons and critical volume.
Figure 7:
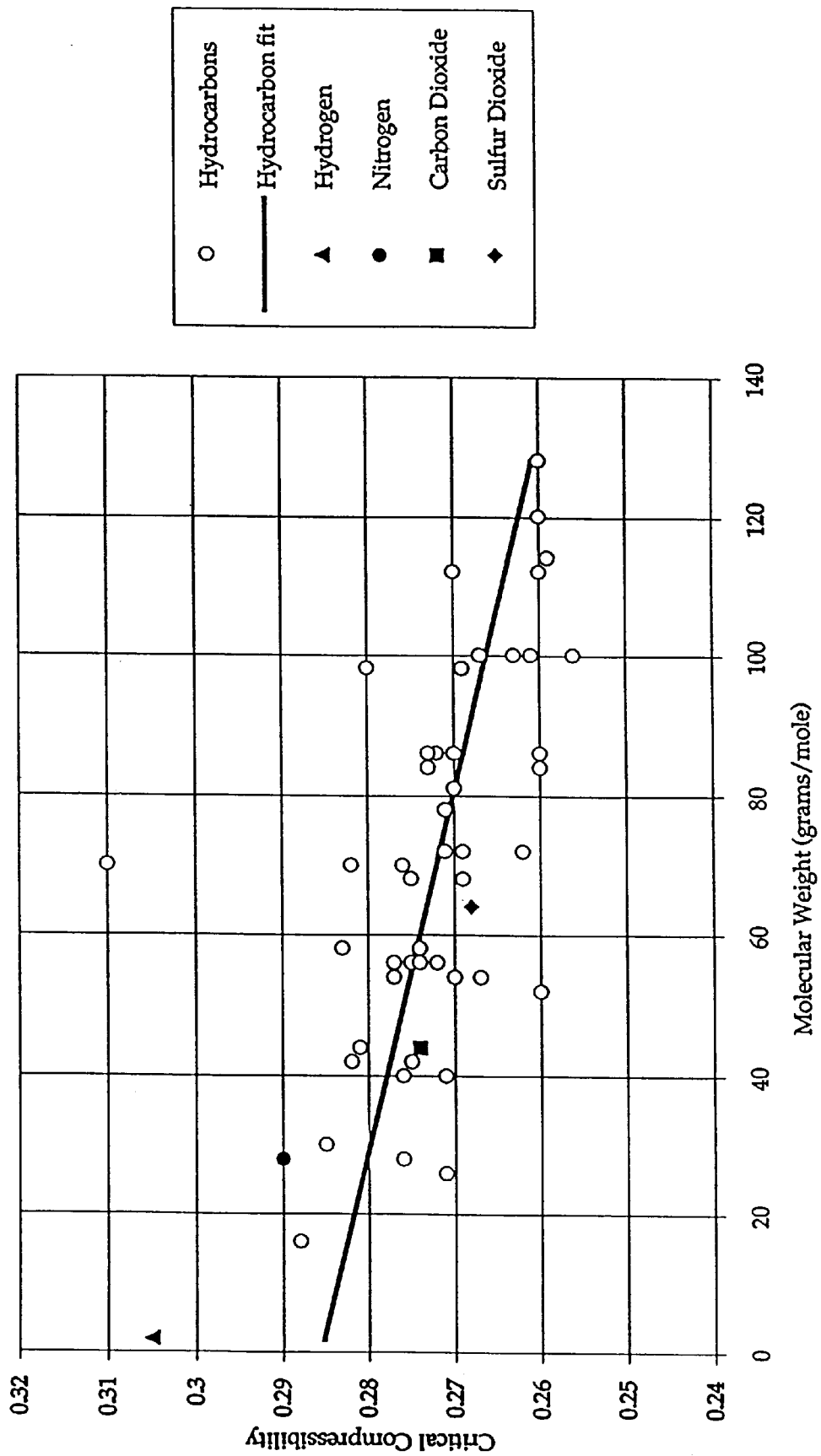
FIG. 7 illustrates a relationship between molecular weight of hydrocarbons and critical compressibility.
Figure 10:
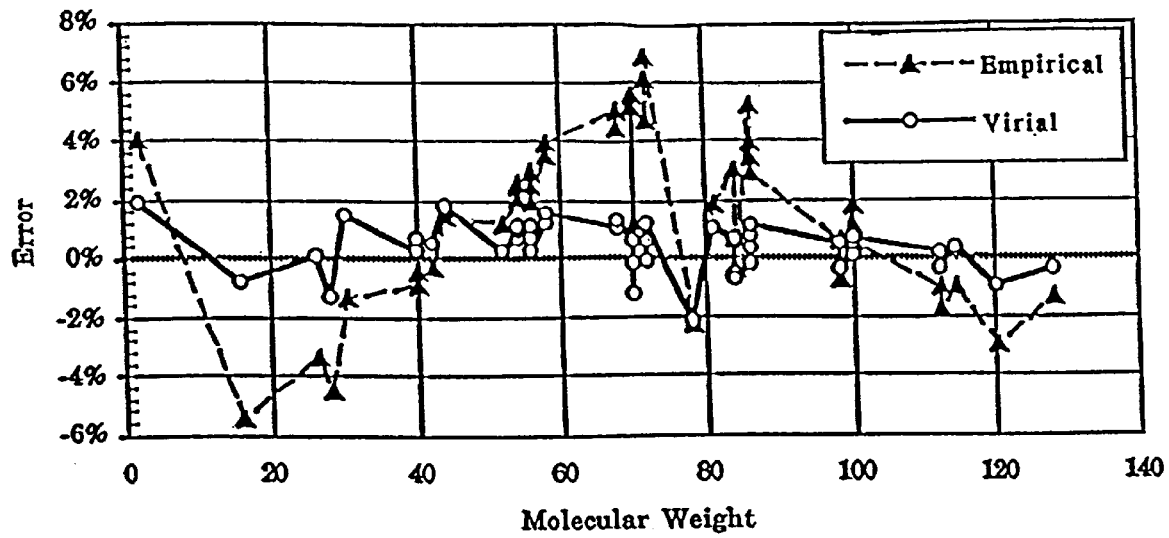
FIG. 10 compares errors using the molecular weight determination of the invention with that of a known protocol for a range of gases.

Errors resulting from application of the virial method to number of hydrocarbons at one atmosphere and 100° F. were tabulated. FIG. 10 compares the errors of this method with the errors resulting from a currently used empirical equation. As shown, the present method yields more accurate results. As seen in FIG. 10, the average error in calculated molecular weights for this set of forty-seven hydrocarbons plus hydrogen was 0.9%.

A further test using experimental sound speed data was made on four natural gases. Here, the virial method was used to calculate a molecular weight from the reported sound speed, and this was compared to the molecular weight determined from the reported composition. For the purpose of calculation, the amounts of inorganic gases in each natural gas were taken as known. These results are shown in Table IV.

TABLE IV

| | MW = 18.41 | | 0° C. | | 30° C. | |
|---|---|---|---|---|---|---|
| Natural Gas 1 composition | | Press. (bar) | calc. M W | error | calc. M W | error |
| CH4 | 81.20% | | | | | |
| C2H6 | 1.05% | 0.01 | 18.36 | −0.27% | 18.32 | −0.49% |

TABLE IV-continued

| | MW = 18.41 | | 0° C. | | 30° C. | |
|---|---|---|---|---|---|---|
| Natural Gas 1 composition | | Press. (bar) | calc. M W | error | calc. M W | error |
| C3H8 | 0.04% | 5 | 18.35 | −0.33% | 18.30 | −0.60% |
| C4H10* | 0.04% | 10 | 18.32 | −0.49% | 18.28 | −0.71% |
| CO2 | 0.49% | 20 | 18.25 | −0.87% | 18.22 | −1.03% |
| N2 | 17.17% | 30 | 18.14 | −1.47% | 18.14 | −1.47% |
| Natural Gas 2 | | | | | | |
| CH4 | 84.50% | | | | | |
| C2H6 | 1.46% | 0.01 | 18.00 | −0.28% | 17.95 | −0.55% |
| C3H8 | 0.06% | 5 | 18.01 | −0.22% | 17.97 | −0.44% |
| C4H10* | 0.06% | 10 | 18.01 | −0.22% | 17.96 | −0.50% |
| CO2 | 0.59% | 20 | 17.94 | −0.61% | 17.91 | −0.78% |
| N2 | 13.34% | 30 | 17.82 | −1.27% | 17.83 | −1.22% |
| Natural Gas 3 | | | | | | |
| CH4 | 82.62% | | | | | |
| C2H6 | 3.47% | 0.01 | 18.64 | 0.16% | 18.58 | −0.16% |
| C3H8 | 0.76% | 5 | 18.63 | 0.11% | 18.57 | −0.21% |
| C4H10* | 0.39% | 10 | 18.60 | −0.05% | 18.55 | −0.32% |
| CO2 | 1.09% | 20 | 18.50 | −0.59% | 18.48 | −0.70% |
| N2 | 11.67% | 30 | 18.36 | −1.34% | 18.38 | −1.24% |
| Natural Gas 11 | | | | | | |
| CH4 | 83.44% | | | | | |
| C2H6 | 9.19% | 0.01 | 19.74 | 1.49% | 19.71 | 1.34% |
| C3H8 | 3.57% | 5 | 19.72 | 1.39% | 19.68 | 1.18% |
| C4H10* | 1.18% | 10 | 19.68 | 1.18% | 19.64 | 0.98% |
| CO2 | 1.91% | 20 | 19.54 | 0.46% | 19.54 | 0.46% |
| N2 | 0.71% | 30 | 19.33 | −0.62% | 19.39 | −0.31% |

The average error shown in TABLE IV for the molecular weights of these natural gases was 0.8%.

The virial method described here uses nonlinear correlations of gas properties with molecular weight. Because of this nonlinearity, a wide distribution of molecular weights in a mixture will give an error in the properties predicted from the average molecular weight. In particular, an increased error occurs when a mixture contains hydrogen. In a Monte Carlo test the average error for mixtures containing hydrogen and four other randomly selected hydrocarbons was 2.3%. The worst error that could be produced by hydrogen in a mixture was found 6.3%, illustratively for a mixture of 85% hydrogen and 15% hexane. Distributions of this range are not commonly encountered, and this distribution-dependence of the calculation will not affect the overall accuracy or utility of the method for practical uses.

RESULTS FOR COMPRESSIBILITY CALCULATIONS

A significant advantage of applicant's virial method is that it also yields the compressibility factor of the gas mixture. This parameter is important for calculating mass flow, particularly at pressures over one atmosphere. For example, for methane at 20 atmospheres, using the compressibility factor increases the calculated mass by 3.4%. For heavier hydrocarbons, the increase would be even larger. Compressibilities z calculated for six gases (solid lines) are shown below in FIG. 12 and are compared with handbook values (dark circles).

Applicant's method actually gives the slope of compressibility with pressure, i.e., a straight line on a graph of compressibility vs. pressure. This works well in the intermediate pressure range for most gases, as shown above. While compressibility of nitrogen is nonlinear in this range, and is not predicted well, advantageously the overall error at 40 bars is not increased if the calculated nitrogen compressibility factor were used.

Thus, the invention accurately determines the average molecular weight of component gases of interest present in a gas, using only parameters such as temperature, pressure and sound speed that are directly and readily measured by ultrasonic interrogation or using simple sensors. The molecular weight may then be used to identify upstream leaks, or sources or events giving rise to the detected hydrocarbon components; or may be used to calculate gas caloric value for furnace or energy capture feed streams; or to otherwise monitor or control flue or feed stream gases of otherwise unknown or poorly controlled composition.

The invention being thus disclosed, further variations and modifications will occur to those skilled in the art, together with adaptations to known process control, monitoring or detection systems. All such variations, modifications and adaptations are considered to be within the scope of the invention, as set forth herein, and defined by the claims appended hereto and equivalents thereof.

What is claimed is:

1. An ultrasonic measurement system for determining a characteristic of material in a conduit or the like, such system comprising:

a plurality of transducer elements arranged for performing a signal path measurement of ultrasonic signals through the material, and a processor for receiving and processing such signals, wherein the processor is configured to determine sound speed and determine average molecular weight of an unknown mixture of hydrocarbons present together with known non-hydrocarbon components in said material, by applying virial equations and mixing rules and comparing calculated results and the determined sound speed.

2. An ultrasonic measurement system according to claim 1, wherein the processor includes a plurality of stored tables of critical constants of hydrocarbon mixtures as function of molecular weight of the mixtures.

3. An ultrasonic measurement system according to claim 2, wherein the processor is configured to iteratively i) set a hypothetical hydrocarbon component molecular weight ii) look up the critical constants of the hypothetical molecular weight, iii) apply virial equations and mixing rules to determine a predicted sound speed for said hypothetical molecular weight hydrocarbon component together with one or more known inorganic components of said fluid material, and iv) repeat said steps ii–iii until the hypothetical molecular weight predicted sound speed is substantially equal to the measured sound speed thereby determining the average molecular weight of said unknown hydrocarbon mixture component.

4. An ultrasonic measurement system according to claim 3, wherein said processor is configured for user input of known quantities of one or more gases selected from among nitrogen, hydrogen, carbon dioxide, sulfur dioxide and other inorganic gases.

5. A system for measurement or control, such system comprising a sound speed detector for measuring sound speed in a fluid, the fluid including a background gas of non-hydrocarbon material of known composition and an unknown mixture of one or more hydrocarbons having an average molecular weight a processor operative with the measured sound speed to determine the average molecular weight by a process of iterative calculation with virial coefficients and mixing rules for the unknown mixture and background gas, and comparison with a measured sound speed.

6. A system according to claim 5, wherein the processor has a stored table of equivalences relating average molecular weight of a mixture of gases with virial coefficients, and the processor applies said table in the iterative calculation to determine at least one critical property of the fluid.

* * * * *